(12) United States Patent
He et al.

(10) Patent No.: US 6,262,327 B1
(45) Date of Patent: Jul. 17, 2001

(54) PROCESS FOR ALKYLATION OF ISOPARAFFIN WITH OLEFIN

(75) Inventors: Yigong He; Fen Li; Enze Min, all of Beijing (CN)

(73) Assignees: China Petrochemical Corporation; Research Institute of Petroleum Processing, SINOPEC, both of Beijing (CH)

( * ) Notice: Subject to any disclaimer, the term of this patent is extended or adjusted under 35 U.S.C. 154(b) by 0 days.

(21) Appl. No.: 09/295,410

(22) Filed: Apr. 21, 1999

(30) Foreign Application Priority Data

Apr. 22, 1998 (CN) .................................................. 98101617

(51) Int. Cl.[7] ................................. C07C 2/56; C07C 2/58
(52) U.S. Cl. .......................... 585/709; 585/722; 585/725; 585/721; 585/732
(58) Field of Search ................................. 585/709, 721, 585/722, 725, 732

(56) References Cited

U.S. PATENT DOCUMENTS

| | | | |
|---|---|---|---|
| 3,549,557 | 12/1970 | Bolton et al. | 502/73 |
| 3,644,565 | 2/1972 | Biale | 585/722 |
| 3,647,916 | 3/1972 | Caesar et al. | 585/722 |
| 3,678,120 | 7/1972 | Bloch | 585/458 |
| 3,852,371 | 12/1974 | Kemp | 585/724 |
| 3,855,342 | 12/1974 | Huang et al. | 585/726 |
| 3,917,738 | 11/1975 | Fenske et al. | 585/722 |
| 3,962,133 | 6/1976 | Rodewwald | 502/181 |
| 4,116,880 | 9/1978 | Olah | 585/722 |
| 4,384,161 | 5/1983 | Huang | 423/659 |
| 5,321,196 * | 6/1994 | Ohgoshi et al. | 585/709 |
| 5,324,881 | 6/1994 | Kresge et al. | 585/721 |

FOREIGN PATENT DOCUMENTS

| | | |
|---|---|---|
| 94120018 | 7/1996 | (CN) . |
| 94120022 | 7/1996 | (CN) . |
| 0433954 | 6/1991 | (EP) . |
| 1389237 | 4/1975 | (GB) . |
| 1432720 | 4/1976 | (GB) . |
| 1245853 | 10/1989 | (JP) . |
| WO9403415 | 2/1994 | (WO) . |
| WO9424075 | 10/1994 | (WO) . |

* cited by examiner

Primary Examiner—Walter D. Griffin
Assistant Examiner—Tam M. Nguyen
(74) Attorney, Agent, or Firm—Birch, Stewart, Kolasch & Birch, LLP (57) ABSTRACT

A process for alkylation of an isoparaffin with an olefin comprising contacting an isoparaffin containing feed with an olefin-containing feed in the presence of a catalyst, said catalyst is a supported heteropoly acid catalyst, which is represented by the following chemical formula: $H_kYW_mMo_{12-n}O_{40} \cdot nH_2O$, wherein k is 3 or 4, Y is an atom of P, Si, Ge or As, m is a positive integer between 0–12, n is any number in the range of >0–10; the reaction temperature is at least equal to the critical temperature of isoparaffin and up to 300° C.; the reaction pressure is at least equal to the critical pressure of isoparaffin. The advantages of this process are embodied in high olefin conversion, high alkylate yield, and good retention of catalyst stability at the same time.

12 Claims, 2 Drawing Sheets

PROCESS FOR ALKYLATION OF ISOPARAFFIN WITH OLEFIN

FIELD OF THE INVENTION

The present invention relates to a process for addition of saturated hydrocarbons with unsaturated hydrocarbons, more particularly, the present invention relates to a process for alkylation of isoparaffin with olefin.

BACKGROUND OF THE INVENTION

In petroleum-chemical industry, sulfuric acid and hydrofluoric acid catalysts are widely used in the process of isoparaffin-olefin alkylation, especially for light isoparaffin and light olefin alkylation, in order to produce higher molecular weight paraffin with high octane rating, as valuable gasoline blending components. However, both sulfuric acid and hydrofluoric acid share inherent drawbacks including equipment corrosion problem, serious environment and safety concerns. A lot of efforts have been made to develop solid acid alkylation catalysts for substitution of sulfuric acid and hydrofluoric acid.

In recent years, new solid acid catalysts for the above alkylation process have been widely investigated and reported. For example, U.S. Pat. No. 3,549,557, U.S. Pat. No. 3,644,565, U.S. Pat. No. 3,647,916, U.S. Pat. No. 3,917,738 and U.S. Pat. No. 4,384,161 discloses catalysts having molecule sieve as active components. JP 01, 245, 853, U.S. Pat. No. 3,962,133 and U.S. Pat. No. 4,116,880, GB 1,432,720 and GB 1,389,237 disclose $SO_4^{2-}$ enhanced super acid catalysts; EP 0,433,954, U.S. Pat. No. 3,678,120, U.S. Pat. No. 3,852,371, and U.S. Pat. No. 3,855,342, WO 94/24075 disclose liquid super acid or supported Lewis acid catalyst etc.. But the deactivation of the above molecular sieve catalysts and solid super active acid catalysts occurs quickly, in a few hours or even less than an hour the olefin conversion reduces dramatically. Besides, the product distributions are not ideal and the problems of halide loosing and equipment corrosion exist with the liquid super acid or supported Lewis acid catalysts.

WO 94/03415 discloses a paraffin-olefin alkylation process comprising contacting an olefin-containing feed with an isoparaffin-containing feed in the presence of a crystalline microporous material under conversion conditions of alkylation, including a temperature at least equal to/or above the critical temperature of said principal component of the feed and a pressure at least equal to/or above the critical pressure of said principal component of the feed. Said zeolites include ZSM series, offretite, MCM, mordenite, REY etc.; said layered material includes layered silicate, layered clays etc.. For example, higher olefin conversion and improved catalyst activity and stability can be obtained with MCM series zeolite catalyst. However, the butene conversion is still quite low, only 86.3–99.4 wt %.

CN 1,125,639A discloses an isobutane-butene alkylation process comprising dissolving $H_3PW_{12}O_{40}$, $H_3PMo_{12}O_{40}$, $H_4SiW_{12}O_{40}$, $H_kPW_{12}Mo_{12-n}O_{40}$(n=1–11) etc. heteropoly acids in light fatty acid, ester, ketone, ether, alcohol or the mixture of fatty acid and fatty alcohol with a concentration of 10–70% to be used as catalyst; the catalytic isobutane-butene alkylation reaction is carried out at 10–70° C. with a paraffin/olefin ratio 1.5–18. Although the equipment corrosion caused by $H_2SO_4$ or HF is avoided, new problem of separating the reaction products from solvent occurs since the reaction is carried out in the liquid phase. Besides, the olefin conversion and the yield of alkylates are relatively low as shown in the Comparative Examples 1–9, the yield of alkylates is only 0.693–1.736 (based on olefin weight) in the batch reactor.

CN 1,125,640A discloses an isobutane-butene alkylation process. The catalyst used in said process is alkali or ammonium salt of heteropoly acid, such as that of phosphorus-tungsten heteropoly acid, phosphorus-molybdenum heteropoly acid, silicon-tungsten heteropoly acid, silicon-molybdenum heteropoly acid; the alkali or ammonium cation range (mole) for phosphorus series is 0.5–3.0, and for silicon series is 0.5–4.0; the reaction temperature is 30° C.; the ratio of isobutane to butene is 15:1. The yield of alkylates is still quite low for said process and the stability of the catalyst activity is not ideal. As in the example, the highest alkylates yield of said alkylation process in batch reactor is 1.854 (based on olefin weight), and the activity reduces with the increase of the reaction times. In said Example 1, the alkylation reaction was carried out in the presence of $Cs_{2.5}H_{0.5}PW_{12}$ catalyst, 0.4378 g olefin and paraffin with a paraffin/olefin ratio of 15 were added to the reactor and reacted at 30° C. for 2 hours; 0.8118 g alkylate oil was obtained with the yield of 1.854. After separating the catalyst and dried at 100° C. for 2 hours the catalyst is reused under the same conditions and the alkylate yield is reduced to 1.384.

U.S. Pat. No. 5,324,881 discloses a process for isoparaffin-olefin alkylation in the presence of a supported heteropoly acid catalyst. Said heteropoly acid contains at least one central element selected from the group consisting of: P, Si, B, Ge, As, Se, Ti, Zr, Mn, F, V, Ce, Th, and at least one coordinating element selected from the group consisting of: Mo, W, V, Mn, Co, Ni, Cu, Zn, Fe. The catalyst used for said process is a supported heteropoly acid catalyst, according to the Example report, all the heteropoly acid catalysts were pretreated above 350° C., the olefin conversion was up to 87 wt % and the highest $C_6^4$ alkylates yield was at most 1.4 g/g2$C_4^-$. It is proved that the stability of the catalyst activity is still not promising by said process.

PURPOSE OF THE INVENTION

An object of the present invention is to overcome the shortcomings of the prior art, such as for example low olefin conversion, low yield of alkylates, and specially, inferior stability of catalyst, and thereby to provide an isoparaffin-olefin alkylation process having higher olefin conversion, higher yield of alkylates and in the mean time, excellent stability of the catalyst, comparing with the other alkylation processes.

BRIEF DESCRIPTION OF THE INVENTION

The present invention found surprisingly that by using a special hetropolyacid as catalyst and proper controlling reaction conditions of the isoparaffin-olefin alkylation, not only the olefin conversion can be higher, but also the running time of catalyst in the alkylation is much longer.

The present invention provides a process for alkylation of an isoparaffin with an olefin by contacting an isoparaffin-containing feed with an olefin-containing feed in the presence of, as catalyst, a supported catalyst comprising of 30–99 wt % porous supporter materials and 1–70 wt % heteropoly acid having the following chemical formula:

$$H_kYW_mMo_{12-m}O_{40}\cdot nH_2O$$

Wherein H is hydrogen atom, k is the number of hydrogen atoms, which is 3 or 4; Y is an atom selected from the group consisting of P, Si, Ge or As; W is tungsten atom, m is the number of tungsten atoms, which is a positive integer between 0–12; Mo is molybdenum atom, 12-m is the number of molybdenum atoms; O is oxygen atom, n is the number of crystal water molecule, which may be any number in the range of >0–10; said reaction temperature is not lower than the critical temperature of the isoparaffin in the feed and at most 300° C.; the reaction pressure is not lower than the critical pressure of the isoparaffin in the feed; said isoparaffin is one or more types of isoparaffin selected from $C_4$–$C_7$ isoparaffins.

DETAILED DESCRIPTION OF THE INVENTION

According to the process provided by the present invention, n in said chemical formula of heteropoly acid is preferably any number between 0.5–6.

According to the process provided by the present invention, the compositions of said catalyst are preferably 45–95 wt % porous supporter material, 5–55 wt % heteropoly acid.

According to the process provided by the present invention, said porous supporter material is selected from inorganic porous supporter materials, organic porous supporter materials or their complex, preferably one or more materials selected from the group consisting of active carbon, alumina, silica, natural or synthetic zeolites, molecular sieve, carbon fiber and clay. Said zeolites or molecular sieve can be selected from zeolite A, zeolite X, zeolite Y, mordenite, ZSM-series zeolite, zeolite Beta, offretite, zeolite $\Omega$, P-Al molecular sieve, Ti—Si molecular sieve or mixtures thereof. Said clay can be non-layered clay, such as kaolin, celite etc., and swelling layered clay, such as montmorillonite, ectorite etc.. Preferably the porous supporter material is selected from active carbon, silica, alumina and zeolites. More preferably the porous supporter material is selected from active carbon, silica or alumina. Although the alkylation of isoparaffin with olefin can be carried out in the presence of low specific surface catalyst, e.g.<100 $m^2$/g, the activity and stability increase with the increase of the surface area of the specific catalyst. Therefore, the specific surface area of said porous supporter material is preferably>100 $m^2$/g.

P atom or Si atom is preferred for Y in said chemical formula of heteropoly acid.

Said isoparaffin containing feed can be pure isoparaffins or isoparaffin and other components that will not affect the alkylation reaction. The content of isoparaffin in the feed can be varied over a fairly broad range. The catalyst used in the present invention is a kind of supported heteropoly acid catalyst, said heteropoly acid contains>0–10 crystal water molecules, preferably 0.5–6, i.e. reaction temperature is not higher than 300° C., more preferably not higher than 250° C. Otherwise, the crystal water in the heteropoly acids will be lost and the effectiveness of the catalyst can not reach the requirement of the present invention. Therefore, the critical temperature of said isoparaffin should not be over 300° C., preferably 250° C. In another words, said isoparaffin should be one or more of isoparaffin selected from the $C_4$–$C_7$ isoparaffins and isoparaffins with higher carbon number are not included in the present invention. For industrial requirements, said isoparaffin is preferably selected from $C_4$–$C_4$ isoparaffins, such as iosbutane, 2-methylbutane, 2-methylpentane, 3-methylpentane, 2,3-dimethylbutane etc., preferably isobutane. The critical temperature and pressure of $C_4$–$C_6$ iosparaffins are listed in Table 1 (from CRC Handbook of Chemistry and Physics, R. C. Weast and D. R. Lide, 1990).

TABLE 1

| Isoparaffin | Critical temperature, ° C. | Critical pressure, atm |
|---|---|---|
| Isobutane | 135 | 35.9 |
| 2-methylbutane | 187.8 | 32.9 |
| 2-methylpentane | 224.3 | 30.0 |
| 3-methylpentane | 224.9 | 30.2 |
| 2,3-dimethylbutane | 226.8 | 30.9 |

Said olefin containing feed can be pure olefins or mixtures of olefin with other components which will not affect the alkylation reaction. The content of olefin in the feed can be varied over a fairly broad range. Said olefin includes all kinds of monoethylene unsaturated olefins with the number of carbon atoms not less than 3. For industrial requirements, said olefin is preferably one or several kinds of olefin selected from the $C_3$–$C_6$ olefins. The position of double bond, e.g. propene, 1-butene, 2-butene, isobutene, 1-pentene, 2-pentene, 2-methyl-1-butene, 2-methyl-2-butene, 3-methyl-1-butene and hexenes, preferably propene, butenes or mixture thereof is not critical.

According to the process provided by the present invention, in order to keep the number of crystal water molecules not more than 10, preferably not more than 6, the water content in the feed should be controlled to not more than 200 ppm, preferably not more then 100 ppm.

According to the process provided by the present invention, said reaction temperature should not lower than the critical temperature of said isoparaffin in the feed, but not higher than 300° C., preferably not higher than 250° C., more preferably not higher than 200° C. Said reaction pressure should not be lower than the critical pressure of said isoparaffin in the feed, when said paraffin is isobutane and said olefin is propene, butene or mixture thereof, said reaction pressure should preferably be 36–100 atm, more preferably 36–90 atm.

According to the process provided by the present invention, said isoparaffin/olefin mole ratio is in the range of 2.0–100, preferably 10–90; WHSV of feed is 0.1–20 $hr^{-1}$, preferably 0.5–8$^{-1}$.

According to the process of alkylation of an isoparaffin with an olefin provided by the present invention, the process can be carried out in all kinds of reactor, such as fixed-, batch-, moving-, fluidized-bed or tri-phase slurry reactor etc.

According to the process provided by the present invention, said catalyst can be prepared by the following procedures:

1. Predetermined amount of supporter powder or formed particulate supporter is treated under low vacuum or atmosphere, at 50–100° C., for 0.5–2 hr, then cooled to room temperature.

2. Predetermined amount of heteropoly acid solution is used to impregnate the above treated supporters under vacuum or atmosphere for 0.5–2 hr;

3. Drying is carried out at 100–300° C., preferably 100–250° C., for 4–10 hr under vacuum or atmosphere with inert gas environment. Said inert gas environment means reaction will not take place between the gas and the heteropoly acid/or support, e.g. nitrogen.

The amount of crystal water in the heteropoly acid is measured by thermogravimetry, the following procedures are used:

About 50 mg of weighted catalyst is put into the sample cell of thermogravimetric analyzer in a stream of 50 ml/min nitrogen, heating the mixture from room temperature to the catalyst drying temperature as prepared, then said temperature is kept constant for the same time as catalyst prepared, record the weight loss of the sample as $W_1$ (wt %). Then the sample is heated at the speed of 10° C./min up to 350° C., record the second weight loss of the sample as $W_2$ (wt %). The number of crystal water molecules in the heteropoly acid is calculated as follows:

$$n=M(W_2-W_1)/N[1-(W_2-W_1)]$$

wherein M is the molecular weight of the heteropoly acid, N is the molecular weight of water. The thermogravimetric analyzer can be any conventional thermogravimetric analyzer. In the present invention a 951 thermogravimetric analyzer of Doupont 2100 thermal analysis system is used.

As compared with the other alkylation processes using solid acid catalysts, the olefin conversion and alkylate yield of the process provided by the present invention are surprisingly high, as well as the stability of the catalyst is excellent. For example, according to the process provided by the present invention, when the reaction conditions as follows:

Reaction temperature 136–198° C.
Reaction pressure 50–85 atm.
Isoparaffin/olefin (mole ratio) 20.7–82.4
WHSV 1–6.32
Catalyst 10–50 wt % $H_3PW_{12}O_{40} \cdot 2H_2O$/active carbon or 50 wt % $H_3PW_{12}O_{40} \cdot 0.8H_2O/Al_2O_3$ or 50 wt % $H_3PW_{12}O_{40} \cdot 4.5H_2O/SiO_2$ or 50 wt % $H_3PMo_{12}O_{40} \cdot 2H_2O$/active carbon or 50 wt % $H_4SiW_{12}O_{40} \cdot 3H_2O$/active carbon butene ($C_4^{32}$) conversion can be as high as 100 wt %, and even after running 56–104 hr the butene conversion still remains unchanged. The yield of $C_5^+$ alkylates reaches 1.94–2.02 (g/g converted butene), nearly approaches the theory value of 2.03 (g/g converted butene). The butene conversion and the yield of $C_5^{30}$ alkylates of the present invention are obviously higher than that of the processes disclosed by WO 94/03415, U.S. Pat. No. 5,324,8812, CN 1125640A and CN 1125639A. But when the reaction conditions change to the reaction temperature and pressure below the critical temperature and pressure of isobutane (120° C., 25 atm), isoparaffin/olefin (mol ratio) 42.8, WHSV 2.31, and 50 wt % $H_3PW_{12}O_{40} \cdot 2H_2O$/active carbon as catalyst, after running 24 hr the butene conversion and alkylates yield drop sharply, and the catalyst deactivates quickly (Table 4).

Figure 1:
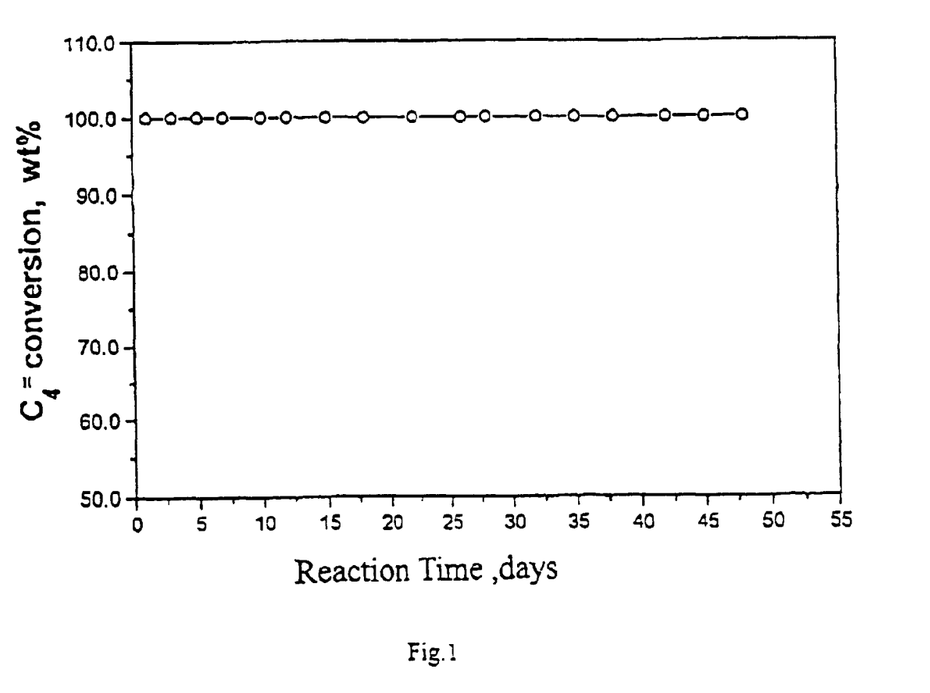
FIG. 1 is a diagram showing the changes in butene conversion with the running time of the isobutane-butene alkylation process provided by the present invention.
Figure 2:
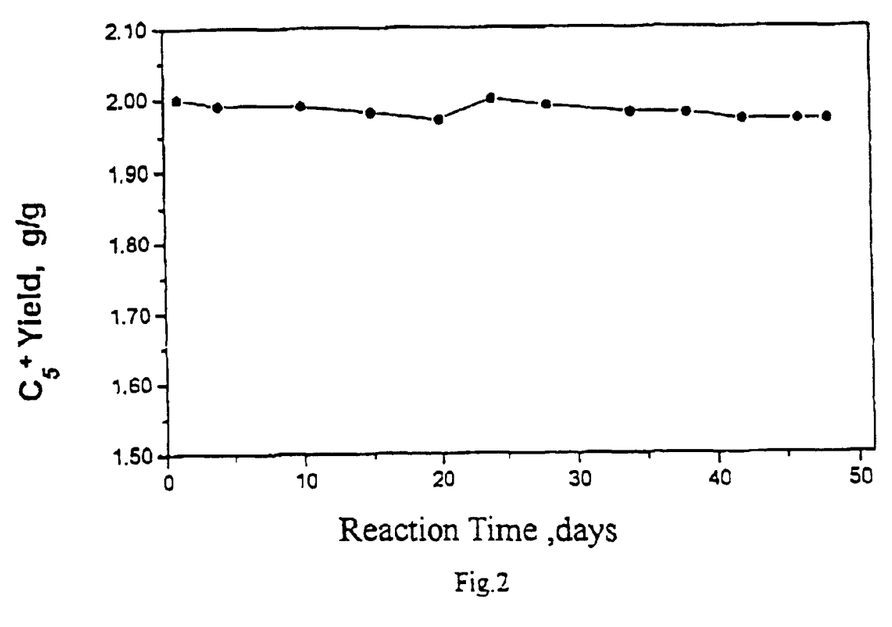
FIG. 2 is a diagram showing the changes in the yield of $C_5^+$ alkylates with the running time of the isobutane-butene alkylation process provided by the present invention.

According to the process provided by the present invention, when isobutane and butene are contacted with 50 wt % $H_3PW_{12}O_{40} \cdot 2H_2O$/active carbon catalyst at a $C_4^0/C_4^-$ mole ratio of 20.0, at a reaction temperature of 136° C., reaction pressure of 40 atm and, WHSV of 2.50, the butene ($C_4$-) conversion can reach 100 wt % and the yield of $C_5^+$ alkylates is nearly 2 g/g converted butene, after running 1150 hr (~48 days), they both still remain unchanged (see FIGS. 1 and 2). But, when a 50 wt % $H_3PW_{12}O_{40} \cdot 12H_2O$/active carbon and 50 wt % $H_3PW_{12}O_{40}$/active carbon catalyst is used, under the same reaction conditions, the butene conversion drops quickly with the prolonging reaction time as shown in Table 5.

Since a pollution-free supported heteropoly acid catalyst is used in the present invention, equipment corrosion caused by sulfuric acid and hydrofluoric acid is avoided, and without environmental contamination. It is a great improvement as compared with the existing industrial sulfuric acid and hydrofluoric acid processes. Besides, according to the process provided by the present invention, higher olefin conversion, higher yield of alkylates and longer running time with good catalyst activity and stability can be obtained as compared with the solid acid catalyst processes. Therefore, it will have a promising future in commercial application.

EXAMPLES

The present invention will be further described with reference to the following samples. However, these examples are not to be construed to limit the scope of the present invention.

The compositions of the feeds of isoparaffin and olefin in the following examples are listed in Table 2.

TABLE 2

| Isobutane Containing Feed | | Butene containing Feed | |
| --- | --- | --- | --- |
| Composition | Content, wt % | Composition | Content, wt % |
| Propane | 1.82 | n,iso-butenes | 2.92 |
| Isobutane | 94.85 | n-butane | 11.62 |
| n-butane | 2.21 | cis-2-butene | 57.70 |
| Butene | 1.12 | Trans-2-butene | 27.76 |
| Water | 34* | Water | 8* |

*ppm

Example 1

An isobutane-butene alkylation was carried out according to the process provided by the present invention.

14.2 g of $H_3PW_{12}O_{40} \cdot 21H_2O$ (analytical grade, manufactured by Beijing Xin Hua Chemical Reagent Plant) was dissolved in 40 ml de-ionized water to form a $H_3PW_{12}O_{40}$ aqueous solution. 12.5 g 20–40 mesh active carbon (manufactured by Beijing Guang Hua Wood Plant) was put into a vacuum vessel and treated under 0.095 MPa and 75° C. for 1 hour, cooled to room temperature and added in $H_3PW_{12}O_{40}$ aqueous solution under vacuum to impregnate for one hour, then dried at 160° C. for 6 hours (still under vacuum). A supported heteropoly acid catalyst with 50 wt % $H_3PW_{12}O_{40} \cdot 2H_2O$ and 50 wt % active carbon was obtained and designated as 50% $H_3PW_{12}O \cdot 2H_2O$/active carbon. The specific surface area of said catalyst was 409 m$^2$/g as determined by low temperature nitrogen adsorption BET method.

1. 10.0 g of said 50% $H_3PW_{12}O_{40} \cdot 2H_2O$/active carbon catalyst was loaded in a fix-bed reactor (25 ml) and was heated in a stream of nitrogen to raise the temperature and pressure to the required conditions. Pre-determined amount of isobutane and butene containing feeds were pumped into the reactor by two precise metering pumps (made by Eldex Lab., Inc, U.S.A.) and the nitrogen stream was switched off at the same time. Vent was analyzed by SP-3420 gas chromatography and the compositions of liquid product were analyzed by HP-5890 gas chromatography from time to time. The compositions of the feeds are listed in Table 2. The reaction conditions and the results are listed in Table 3.

Comparative Example 1

Isobutane-butene alkylation with sulfuric acid catalyst was carried out 73.3 g 95 wt % sulfuric acid (analytical grade, manufactured by Beijing Li Sui Chemical Plant) was added into an autoclave, then 18.0 g isobutane-containing feed and 3.48 g butene-containing feed were added into the reactor with strong stirring at 10° C., 0.7 MPa. Said reaction was carried on for 2 hours. The compositions of the gas-phase products we analyzed by SP-3420 gas chromatography and the compositions of liquid product were analyzed by HP-5890 gas chromatography. The compositions of the feeds are listed in Table 2. The reaction conditions and the results are listed in Table 3.

Comparative Example 3

This comparative example is to indicate the situation with heteropoly acid catalyst with crystal water number not in the range of the present invention.

Said isobutane-butene alkylation was carried out according to the same reaction conditions as Example 1, but with a different catalyst. A supported heteropoly acid catalyst with 50 wt % $H_3PW_{12}O_{40} \cdot 12H_2O$ and 50 wt % active carbon was used and designated as 50% $H_3PW_{12}O_{40} \cdot 12H_2O$/active

TABLE 3

| Catalyst | 50% $H_3PW_{12}O_{40} \cdot 2H_2O$/active carbon | | | | | | | 95% $H_2SO_4$ |
|---|---|---|---|---|---|---|---|---|
| Reaction Temp., ° C. | 136.0 | | | | | | | 10.0 |
| Reaction Pressure, atm | 50.0 | | | | | | | 7.0 |
| $C_4^\circ/C_4^-$ (mole ratio) | 42.8 | | | | | | | 6.0 |
| WHSV, $hr^{-1}$ | 2.31 | | | | | | | — |
| Reaction Time, hr | 6 | 12 | 24 | 48 | 72 | 82 | 104 | 2 |
| $C_4^-$conversion, wt % | 100 | 100 | 100 | 100 | 100 | 100 | 100 | 100 |
| $C_5^+$yield, g/g converted $C_4^-$ | 2.01 | 2.02 | 2.00 | 1.98 | 1.99 | 2.02 | 2.00 | 2.00 |
| $C_5^+$product distribution, wt % | 0.91 | | 1.67 | 1.40 | | 1.32 | 1.04 | 0.20 |
| $C_5$ | | | | | | | | |
| $C_6$ | 1.23 | | 1.58 | 1.85 | | 1.23 | 1.46 | 1.10 |
| $C_7$ | 3.64 | | 2.99 | 2.12 | | 3.45 | 2.74 | 2.80 |
| $C_8$ | 69.58 | | 68.71 | 67.64 | | 67.01 | 66.81 | 73.80 |
| $C_9^+$ | 24.66 | | 25.05 | 26.99 | | 26.99 | 27.95 | 21.40 |
| $C_8^-$ | 0.00 | | 0.00 | 0.00 | | 0.00 | 0.00 | 0.00 |

Comparative Example 2

This comparative example is to show the advantages of the process provided by the present invention.

An isobutane-butene alkylation was carried out below the critical temperature and pressure of the isoparaffin. The amount of catalyst, feeds, reaction system and analytical methods were same as Example 1, except that the reaction conditions were as follows: a reaction temperature of 120° C., a reaction pressure of 25.0 atm, $C_4^\circ/C_4^-$ (mole ratio) 42.8, WHSV 2.31 $hr^{-1}$. The reaction conditions and the results are listed in Table 4.

TABLE 4

| Catalyst | 50% $H_3PW_{12}O_{40} \cdot 2H_2O$/active carbon | | | | | |
|---|---|---|---|---|---|---|
| Reaction Temp., ° C. | 120.0 | | | | | |
| Reaction Pressure, atm | 25.0 | | | | | |
| $C_4^\circ/C_4^-$ (mole ratio) | 42.8 | | | | | |
| WHSV, $hr^{-1}$ | 2.31 | | | | | |
| Reaction Time, hr | 6 | 12 | 24 | 32 | 48 | 56 |
| $C_4^-$conversion, wt % | 100 | 100 | 100 | 85.9 | 74.6 | 70.8 |
| $C_5^+$yield, g/g converted $C_4^-$ | 2.01 | 2.02 | 1.99 | 1.68 | 1.51 | 1.48 |
| $C_5^+$ distribution, wt % | 1.32 | 1.04 | 0.98 | 0.56 | 0.41 | 1.32 |
| $C_5$ | | | | | | |
| $C_6$ | 1.67 | 1.75 | 1.61 | 1.24 | 1.09 | 1.11 |
| $C_7$ | 3.42 | 2.11 | 2.31 | 1.89 | 1.46 | 1.52 |
| $C_8$ | 67.40 | 65.90 | 65.20 | 56.61 | 50.54 | 46.30 |
| $C_9^+$ | 26.20 | 29.20 | 29.90 | 32.40 | 35.90 | 37.75 |
| $C_8^-$ | 0.00 | 0.00 | 0.00 | 7.30 | 10.60 | 12.00 | carbon. Said catalyst was prepared by nearly the same procedures as Example 1, except that the final drying conditions were at 60° C. for 1 hour. The test results of said isobutane-butene alkylation are listed in Table 5.

Comparative Example 4

This comparative example is used to indicate the situation of heteropoly acid catalyst with crystal water number not in the range of the present invention.

Said isobutane-butene alkylation was carried out according to nearly the same conditions as Example 1, but with a different catalyst. A supported heteropoly acid catalyst with 50 wt % $H_3PW_{12}O_{40}$ and 50 wt % active carbon was used and designated as 50% $H_3PW_{12}O_{40}$/active carbon. Said catalyst was prepared by nearly the same procedures as Example 1, except that the final drying conditions were at 350° C. for 1 hour. The test results of said isobutane-butene alkylation are listed in Table 5.

TABLE 5

| Catalyst | 50% $H_3PW_{12}O_{40} \cdot 12H_2O$/active carbon | 50% $H_3PW_{12}O_{40}$/active carbon |
|---|---|---|
| Reaction Temp., ° C. | 136.0 | 136.0 |
| Reaction Pressure, atm | 50.0 | 50.0 |

TABLE 5-continued

| Catalyst | 50% $H_3PW_{12}O_{40} \cdot 12H_2O$/ active carbon | | | | 50% $H_3PW_{12}O_{40}$/ active carbon | | | |
|---|---|---|---|---|---|---|---|---|
| $C_4^o/C_4^-$ (mole ratio) | 42.8 | | | | 42.8 | | | |
| WHSV, $hr^{-1}$ | 2.31 | | | | 2.31 | | | |
| Reaction Time, hr | 2 | 8 | 19 | 28 | 2 | 8 | 18 | 30 |
| $C_4^-$ conversion, wt % | 100 | 89.8 | 79.5 | 68.4 | 100 | 87.4 | 78.2 | 64.4 |
| $C_5^+$ yield g/g converted $C_4^-$ | 1.85 | 1.72 | 1.64 | 1.51 | 1.82 | 1.70 | 1.60 | 1.52 |
| $C_5^+$ product distributions, wt % | | | | | | | | |
| $C_5$ | 1.52 | 1.31 | 1.02 | 0.89 | 1.49 | 1.24 | 1.11 | 0.92 |
| $C_6$ | 1.72 | 1.64 | 1.50 | 1.30 | 1.81 | 1.63 | 1.47 | 1.28 |
| $C_7$ | 3.24 | 3.01 | 2.94 | 2.61 | 3.67 | 3.44 | 3.00 | 2.54 |
| $C_8$ | 65.40 | 64.51 | 60.16 | 54.66 | 64.70 | 63.11 | 59.49 | 53.60 |
| $C_9^+$ | 18.72 | 19.12 | 19.15 | 22.00 | 19.13 | 19.38 | 19.99 | 22.42 |
| $C_8^-$ | 9.40 | 10.41 | 15.23 | 18.60 | 9.2 | 11.20 | 14.94 | 19.24 |

It can be seen from the results in Tables 3–5 that the butene conversion can reach 100 wt % and can remain unchanged after running over 100 hours according to the process provided by the present invention. If the reaction temperature and pressure is below the critical temperature and pressure of isobutane although using the catalyst provided by the present invention, after running for 24 hours the butene conversion drops sharply and the catalyst deactivates quickly. It can also be seen from the results of Tables 3–5 that the butene conversion and the catalyst activity drop quickly if the number of crystal water of the heteropoly acid catalyst is not in the range of the present invention (i.e. 0 or >10). In such cases, though under the reaction conditions provided by the present invention, the results are not as effective as that of the present invention, indicating that the present invention is superior to the prior arts.

Example 2

An isobutane-butene alkylation ws carried out according to the process provided by the present invention.

The reaction equipment, feeds and catalyst were the same as in Example 1. The following reaction conditions were used:

starting temperature 136.0° C., pressure 50.0 atm; after running for 10 hours the pressure was raised to 85 atm, temperature remained unchanged; running til 36 hours the pressure was reduced to 50 atm and the temperature was raised to 198° C.; and running til 58 hours, the reaction temperature was reduced to 136° C.

The results and the reaction conditions are listed in Table 6.

TABLE 6

| Catalyst | 50% $H_3PW_{12}O_{40} \cdot 2H_2O$ / active carbon | | | |
|---|---|---|---|---|
| Reaction Temp., ° C. | 136.0 | 136.0 | 198.0 | 136.0 |
| Reaction Pressure, atm | 50.0 | 85.0 | 50.0 | 50.0 |
| $C_4^o/C_4^-$ (mole ratio) | 42.5 | 42.5 | 42.5 | 42.5 |
| WHSV, $hr^{-1}$ | 2.30 | 2.30 | 2.30 | 2.30 |
| Reaction Time, hr | 10 | 36 | 58 | 84 |
| $C_4^-$ conversion, wt % | 100 | 100 | 100 | 100 |
| $C_5^+$ yield g/g converted $C_4^-$ | 2.02 | 2.01 | 2.02 | 2.00 |
| $C_5^+$ distribution, wt % | 1.15 | 2.10 | 1.67 | 1.21 |
| $C_5$ | | | | |
| $C_6$ | 1.12 | 1.79 | 1.04 | 1.25 |
| $C_7$ | 3.24 | 3.54 | 2.79 | 2.84 |
| $C_8$ | 67.75 | 70.45 | 67.98 | 68.78 |
| $C_9^+$ | 26.74 | 22.12 | 26.52 | 25.92 |
| $C_8^-$ | 0.00 | 0.00 | 0.00 | 0.00 |

Example 3

An isobutane-butene alkylation was carried out according to the process provided by the present invention.

The reaction equipment, feeds and catalyst were the same as in Example 1. The following reaction conditions were used:

starting: $C_4^o/C_4^-$ (mole ratios) 43.0, WhSV 2.30 $hr^{-1}$;

running till 24 hours: $C_4^o/C_4^-$ (mole ratio) 43.0, WHSV 1.00 $hr^{-1}$;

running till 36 hours: $C_4^o/C_4^-$ (mole ratio) 43.0, WHSV 6.32 $hr^{-1}$;

running till 48 hours: $C_4^o/C_4^-$ (mole ratio) 20.7, WHSV 2.30 $hr^{-1}$;

running till 56 hours: $C_4^o/C_4^-$ (mole ratio) 82.4, WHSV 2.30 $hr^{-1}$;

running till 72 hours: $C_4^o/C_4^-$ (mole ratio) 43.0, WHSV 2.30 $hr^{-1}$.

The results and the reaction conditions are listed in Table 7.

TABLE 7

| Catalyst | 50% $H_3PW_{12}O_{40} \cdot 2H_2O$/active carbon | | | | | |
|---|---|---|---|---|---|---|
| Reaction Temp., ° C. | 136.0 | 136.0 | 136.0 | 136.0 | 136.0 | 136.0 |
| Reaction Pressure, atm | 50.0 | 50.0 | 50.0 | 50.0 | 50.0 | 50.0 |
| $C_4^o/C_4^-$ (molar ratio) | 43.0 | 43.0 | 43.0 | 20.7 | 82.4 | 43.0 |
| WHSV, $hr^{-1}$ | 2.30 | 1.00 | 6.32 | 2.30 | 2.30 | 2.30 |
| Reaction Time, hr | 24 | 36 | 48 | 56 | 72 | 92 |
| $C_4^-$ conversion, wt % | 100 | 100 | 100 | 100 | 100 | 100 |
| $C_5^+$ yield g/g converted $C_4^-$ | 2.02 | 2.01 | 2.01 | 2.00 | 2.01 | 2.00 |
| $C_5^+$ distribution, wt % | 1.09 | 1.01 | 1.12 | 1.24 | 0.98 | 1.20 |

TABLE 7-continued

| Catalyst | 50% $H_3PW_{12}O_{40} \cdot 2H_2O$/active carbon | | | | | |
|---|---|---|---|---|---|---|
| $C_5$ | | | | | | |
| $C_6$ | 1.07 | 0.84 | 2.32 | 2.72 | 0.89 | 1.10 |
| $C_7$ | 3.14 | 2.52 | 3.75 | 3.84 | 2.47 | 3.21 |
| $C_8$ | 69.58 | 73.96 | 66.41 | 68.59 | 73.46 | 70.81 |
| $C_9^+$ | 25.12 | 21.67 | 26.40 | 23.61 | 22.20 | 23.68 |
| $C_8^-$ | 0.00 | 0.00 | 0.00 | 0.00 | 0.00 | 0.00 |

Examples 4–5

The reactions of isobutane-butene alkylation were carried out according to the process provided by the present invention.

Preparation of 10% $H_3PW_{12}O_{40} \cdot 2H_2O$/active carbon:

1.57 g of $H_3PW_{12}O_{40} \cdot 21H_2O$ (same as Example 1) was dissolved in 40 ml de-ionized water to form a $H_3PW_{12}O_{40}$ solution. 12.5 g 20–40 mesh active carbon (same as Example 1) was put in a vacuum vessel and treated under 0.095 MPa and 75° C. for 1 hour, cooled to room temperature and added in $H_3PW_{12}O_{40}$ solution under vacuum to impregnate for one hour, then dried at 160° C. for 6 hours (still under vacuum). A supported heteropoly acid catalyst with 10 wt % $H_3PW_{12}O_{40} \cdot 2H_2O$ and 90 wt % active carbon was obtained and designated as 10% $H_3PW_{12}O_{40} \cdot 2H_2O$/active carbon. The specific surface area of said catalyst was 674 m²/g.

Preparation of 20% $H_3PW_{12}O_{40} \cdot 2H_2O$/active carbon:

Same as the preparation of 10% $H_3PW_{12}O_{40} \cdot 2H_2O$/active carbon, only 3.55 g of $H_3PW_{12}O_{40} \cdot 21H_2O$ was used instead of 1.57 g. A supported heteropoly acid catalyst with 20 wt % $H_3PW_{12}O_{40} \cdot 2H_2O$ and 80 wt % active carbon was obtained and designated as 20% $H_3PW_{12}O_{40} \cdot 2H_2O$/active carbon. The specific surface area of said catalyst was 592 m²/g.

the reactions of isobutane-butene alkylation were carried out according to the same test conditions as Example 1 with 10% $H_3PW_{12}O_{40} \cdot 2H_2O$/active carbon catalyst and 20% $H_3PW_{12}O_{40} \cdot 2H_2O$/active-carbon catalyst, respectively. The results and the reaction conditions are listed in Table 8.

TABLE 8

| Catalyst | 10% $H_3PW_{12}O_{40} \cdot 2H_2O$/active carbon | 20% $H_3PW_{13}O_{40} \cdot 2H_2O$/active carbon |
|---|---|---|
| Reaction Temp., °C. | 136.0 | 136.0 |
| Reaction Pressure, atm | 50.0 | 50.0 |
| $C_4°/C_4^-$ (mole ratio) | 43.8 | 43.81 |
| WHSV, hr⁻¹ | 2.30 | 2.30 |
| Reaction Time, hr | 76 | 78 |
| $C_4^-$ Conversion, wt % | 100 | 100 |
| $C_5^+$ yield g/g Converted $C_4^-$ | 2.01 | 2.00 |
| $C_5^+$ distribution, wt % | 1.67 | 1.08 |
| $C_5$ | | |
| $C_6$ | 1.58 | 1.67 |
| $C_7$ | 2.99 | 3.81 |
| $C_8$ | 67.71 | 69.12 |
| $C_9^+$ | 26.05 | 24.32 |
| $C_8^-$ | 0.00 | 0.00 |

Example 6

An isobutane-butene alkylation was carried out according to the process provided by the present invention.

14.2 g of $H_3PW_{12}O_{40} \cdot 21H_2O$ (same as Example 1) was dissolved in 50 ml de-ionized water to form a $H_3PW_{12}O_{40}$ solution. 12.5 g (dry based) γ-alumina (with a specific surface area of 241 m²/g, manufactured by Catalyst Plant of Changling Petrochemical Works) was put in a vacuum vessel and treated under 0.095 MPa and 75° C. for 1 hour, cooled to room temperature and added in said $H_3PW_{12}O_{40}$ solution under vacuum to impregnate for 1.5 hours, then dried at 230° C. for 6 hours (still under vacuum). A supported heteropoly acid catalyst with 50 wt % $H_3PW_{12}O_4 \cdot 0.8H_2O$ and 50 wt % γ-alumina was obtained and designated as 50% $H_3PW_{12}O_{40} \cdot 0.8H_2O/Al_2O_3$. The specific surface area of said catalyst is 126 m²/g.

The reaction of isobutane-butene alkylation was carried out according to the same test conditions as Example 1 with 50% $H_3PW_{12}O_{40} \cdot 0.8H_2O/Al_2O_3$ catalyst. The results and the reaction conditions are listed in Table 9.

TABLE 9

| Catalyst | 50% $H_3PW_{12}O_{40} \cdot 0.8H_2O/Al_2O_3$ | | | | |
|---|---|---|---|---|---|
| Reaction Temp., °C. | 136.0 | | | | |
| Reaction Pressure, atm | 50.0 | | | | |
| $C_4°/C_4^-$ (mole ratio) | 48.0 | | | | |
| WHSV, hr⁻¹ | 2.51 | | | | |
| Reaction Time, hr | 8 | 24 | 48 | 72 | 80 |
| $C_4^-$ Conversion, wt % | 100 | 100 | 100 | 100 | 100 |
| $C_5^+$ yield g/g Converted $C_4^-$ | 2.02 | 2.01 | 2.01 | 1.99 | 2.00 |
| $C_5^+$ distribution wt % | 0.89 | 1.22 | 1.34 | 1.14 | 1.42 |
| $C_5$ | | | | | |
| $C_6$ | 1.68 | 1.94 | 1.82 | 1.62 | 1.75 |
| $C_7$ | 2.14 | 2.29 | 1.99 | 1.86 | 2.05 |
| $C_8$ | 74.88 | 71.18 | 71.29 | 73.02 | 71.64 |
| $C_9^+$ | 20.41 | 23.37 | 23.56 | 22.36 | 23.14 |
| $C_8^-$ | 0.00 | 0.00 | 0.00 | 0.00 | 0.00 |

Example 7

An isobutane-butene alkylation was carried out according to the process provided by the present invention.

14.2 g of $H_3PW_{12}O_{40} \cdot 21H_2O$ (same as Example 1) was dissolved in 50 ml de-ionized water to form a $H_3PW_{12}O_{40}$ solution. 12.5 g (dry based) large pore silica (specific surface area 418 m²/g, manufactured by Qing Dao Oceanic Chemical Plant) was put in a vacuum vessel and treated under 0.095 MPa and 75° C. for 1 hour, cooled to room temperature and added in said $H_3PW_{12}O_{40}$ solution under vacuum to impregnate for 1.5 hours, then dried at 130° C. for 1.5 hours (still under vacuum). A supported heteropoly acid catalyst with 50 wt % $H_3PW_{12}O_{40} \cdot 4.5H_2O/Al_2O_3$ and 50 wt % silica was obtained and designated as 50% $H_3PW_{12}O_{40} \cdot 4.5H_2O/SiO_2$. The specific surface area of said catalyst is 188 m²/g.

The reaction of isobutane-butene alkylation was carried out according to the same test conditions as Example 1 with 50% $H_3PW_{12}O \cdot 4.5H_2O/SiO_2$ catalyst. The results and the reaction conditions are listed in Table 10.

TABLE 10

| Catalyst | 50% $H_3PW_{12}O_{40} \cdot 4.5H_2O/SiO_2$ | | | | | |
|---|---|---|---|---|---|---|
| Reaction Temp., °C. | 136.0 | | | | | |
| Reaction Pressure, atm | 50.0 | | | | | |
| $C_4°/C_4^-$ (mole ratio) | 48.0 | | | | | |
| WHSV, hr⁻¹ | 2.51 | | | | | |
| Reaction Time, hr | 8 | 24 | 36 | 48 | 72 | 80 |
| $C_4^-$ Conversion, | 100 | 100 | 100 | 100 | 100 | 100 |

TABLE 10-continued

| Catalyst | 50% $H_3PW_{12}O_{40}·4.5H_2O/SiO_2$ | | | | | |
|---|---|---|---|---|---|---|
| wt % | | | | | | |
| $C_5^+$ yield g/g converted $C_4^-$ | 2.02 | 2.01 | 2.00 | 1.99 | 2.01 | 2.00 |
| $C_5^+$ distribution, wt % | 1.78 | 1.19 | 1.21 | 1.02 | 0.51 | 0.64 |
| $C_5$ | | | | | | |
| $C_6$ | 8.14 | 8.11 | 6.21 | 5.20 | 3.96 | 4.12 |
| $C_7$ | 6.24 | 5.04 | 4.74 | 4.56 | 3.69 | 3.49 |
| $C_8$ | 64.57 | 64.63 | 66.42 | 67.08 | 68.41 | 69.31 |
| $C_9^+$ | 19.27 | 21.03 | 21.42 | 22.14 | 23.43 | 22.44 |
| $C_8^-$ | 0.00 | 0.00 | 0.00 | 0.00 | 0.00 | 0.00 |

Example 8

An isobutane-butene alkylation was carried out according to the process provided by the present invention.

14.6 g of $H_3PMo_{12}O_{40}·17H_2O$ (analytical grade, manufactured by Beijing Xin Hua Chemical Reagent Plant) was dissolved in 40 ml de-ionized water to form a $H_3PMo_{12}O_{40}$ solution. 12.5 g (dry based) active carbon (same as Example 1) was put in a vacuum vessel and treated under 0.095 MPa and 75° C. for 1 hour, cooled to room temperature and added in said $H_3PMo_{12}O_{40}$ solution under vacuum to impregnate for 1.5 hours, then dried at 170° C. for 6 hours (still under vacuum). A supported heteropoly acid catalyst with 50 wt % $H_3PMo_{12}O_{40}·2H_2O$ and 50 wt % active carbon was obtained and designated as 50% $H_3PMo_{12}O_{40}·2H_2O$/active carbon. The specific surface area of said catalyst was 421 m²/g.

The reactions of isobutane-butene alkylation were carried out according to the same test conditions as Example 1 with 50% $H_3PMo_{12}O_{40}·2H_2O$/active carbon catalyst. The results and the reaction conditions are listed in Table 11.

TABLE 11

| Catalyst | 50% $H_3PMo_{12}O_{40}.2H_2O$/active carbon |
|---|---|
| Reaction Temp., ° C. | 136.0 |
| Reaction Pressure, atm | 50.0 |
| $C_4°/C_4^-$ (mole ratio) | 47.6 |

TABLE 11-continued

| Catalyst | 50% $H_3PMo_{12}O_{40}.2H_2O$/active carbon | | | | |
|---|---|---|---|---|---|
| WHSV, hr⁻¹ | | | 2.50 | | |
| Reaction Time, hr | 8 | 24 | 36 | 48 | 58 |
| $C_4^-$ Conversion, wt % | 100 | 100 | 100 | 100 | 100 |
| $C_5^+$ yield g/g Converted $C_4^-$ | 1.99 | 1.98 | 1.97 | 1.96 | 1.97 |
| $C_5^+$ distribution, wt % | 0.40 | 0.60 | 0.70 | 0.40 | 0.30 |
| $C_5$ | | | | | |
| $C_6$ | 0.50 | 0.80 | 0.70 | 0.60 | 0.50 |
| $C_7$ | 1.20 | 1.80 | 1.90 | 2.10 | 1.70 |
| $C_8$ | 71.10 | 66.90 | 62.60 | 62.00 | 63.10 |
| $C_9^+$ | 26.80 | 29.90 | 34.10 | 34.90 | 34.40 |
| $C_8^-$ | 0.00 | 0.00 | 0.00 | 0.00 | 0.00 |

Comparative Example 5

This comparative example is used to indicate the reaction results with the catalyst not in the range provided by the present invention.

An isobutane-butene alkylation was carried out according to the process provided as Example 8, but with a different catalyst. Said catalyst was prepared according to the procedures provided in Example 8 for the preparation of catalyst 50% $H_3PMo_{12}O_{40}·2H_2O$/active carbon except that the final drying temperature was changed to 50° C. for 2 hours. Said catalyst comprised 50 wt % $H_3PMo_{12}O_{40}·12H_2O$ and 50 wt % active carbon and was designated as $H_3PMo_{12}O_{40}·12H_2O$/active carbon. The alkylation results are listed in Table 12.

Comparative Example 6

This comparative example is used to indicate the reaction results with the catalyst not in the range provided by the present invention.

An isobutane-butene alkylation was carried out according to the process provided as Example 8, but with a different catalyst. Said catalyst ws prepared according to the procedures provided in Example 8 for the preparation of catalyst 50% $H_3PMo_{12}O_{40}·2H_2O$/active carbon, except that the final drying temperature was changed to 350° C. for 1 hour. Said catalyst comprised 50 wt % $H_3PMo_{12}O_{40}$ and 50 wt % active carbon and was designated as $H_3PMo_{12}O_{40}$/active carbon. The alkylation results are listed in Table 12.

TABLE 12

| Catalyst | $H_3PMo_{12}O_{40}·12H_2O$/ active carbon | | | | $H_3PMo_{12}O_{40}$/ active carbon | | | |
|---|---|---|---|---|---|---|---|---|
| Reaction Temp., ° C. | 136.0 | | | | 136.0 | | | |
| Reaction Pressure, atm | 50.0 | | | | 50.0 | | | |
| $C_4°/C_4^-$ (mole ratio) | 47.6 | | | | 47.6 | | | |
| WHSV, hr⁻¹ | 2.50 | | | | 2.50 | | | |
| Reaction Time, hr | 3 | 10 | 22 | 38 | 2 | 8 | 19 | 36 |
| $C_4^-$ Conversion, wt % | 100 | 91.1 | 79.2 | 64.8 | 100 | 90.2 | 78.7 | 63.1 |
| $C_5^+$ yield g/g converted $C_4^-$ | 1.87 | 1.75 | 1.62 | 1.40 | 1.79 | 1.70 | 1.61 | 1.40 |
| $C_5^+$ distribution, wt % | 1.64 | 1.52 | 1.42 | 1.02 | 1.54 | 1.41 | 1.33 | 1.22 |
| $C_5$ | | | | | | | | |
| $C_6$ | 1.81 | 1.74 | 1.68 | 1.50 | 1.79 | 1.67 | 1.45 | 1.27 |
| $C_7$ | 3.36 | 3.11 | 2.82 | 2.72 | 4.21 | 3.48 | 2.78 | 2.66 |
| $C_8$ | 67.24 | 65.18 | 61.40 | 55.70 | 66.92 | 62.84 | 58.44 | 51.44 |
| $C_9^+$ | 17.17 | 19.24 | 20.62 | 23.14 | 16.84 | 18.29 | 19.90 | 24.19 |
| $C_8^-$ | 8.78 | 9.21 | 12.06 | 15.92 | 8.70 | 12.31 | 16.10 | 19.22 |

Example 9

An isobutane-butene alkylation was carried out according to the process provided by the present invention.

13.67 g of $H_4SiW_{12}O_{40} \cdot 15H_2O$ (analytical grade, manufactured by the Shanghai No. 2. Chemical Reagent Plant) was dissolved in 40 ml de-ionized water to form a $H_4SiW_{12}O_{40}$ solution. 12.5 g active carbon (same as Example 1) was put into a vacuum vessel and treated under 0.095 MPa and 70° C. for 1 hour, cooled to room temperature and added in said $h_4SiW_{12}O_{40}$ solution under vacuum to impregnate for 1.5 hours, then dried at 145° C. for 6 hours (still under vacuum). A supported heteropoly acid catalyst with 50 wt % $H_4SiW_{12}O_{40} \cdot 3H_2O$ and 50 wt % active carbon was obtained and designated as 50% $H_4SiW_{12}O_{40} \cdot 3H_2O$/active carbon. The specific surface area of said catalyst was 434 $m^2/g$.

The reaction of isobutane-butene alkylation was carried out according to the same test conditions as Example 1 with 50% $H_3SiW_{12}O_{40} \cdot 3H_2O$/active carbon catalyst. The results and the reaction conditions are listed in Table 13.

TABLE 13

| Catalyst | 50% $H_4SiW_{12}O_{40} \cdot 3H_2O$ /active carbon | | | | |
|---|---|---|---|---|---|
| Reaction Temp., ° C. | | | 136.0 | | |
| Reaction Pressure, atm | | | 50.0 | | |
| $C_4^o/C_4^-$ (mole ratio) | | | 45.6 | | |
| WHSV, $hr^{-1}$ | | | 2.45 | | |
| Reaction Time, hr | 8 | 24 | 36 | 48 | 56 |
| $C_4^-$ Conversion, wt % | 100 | 100 | 1.00 | 100 | 100 |
| $C_5^+$ yield g/g converted $C_4^-$ | 1.98 | 1.98 | 1.96 | 1.95 | 1.94 |
| $C_5^+$ distribution wt % | | | | | |
| $C_5$ | 0.65 | 0.75 | 0.98 | 0.96 | 1.31 |
| $C_6$ | 0.80 | 0.69 | 0.96 | 1.12 | 1.56 |
| $C_7$ | 1.94 | 1.88 | 2.12 | 2.50 | 2.70 |
| $C_8$ | 67.63 | 63.78 | 59.38 | 57.17 | 54.56 |
| $C_9^+$ | 28.98 | 32.90 | 36.56 | 38.25 | 39.87 |
| $C_8^-$ | 0.00 | 0.00 | 0.00 | 0.00 | 0.00 |

Example 10

This example is to further indicate the stability of the process provided by the present invention.

The reaction system, feeds, catalyst and the amount thereof were the same as in Example 1, but the reaction conditions were different:

Reaction temperature: 136° C.

Reaction pressure: 40 atm

Isobutane/butene (mole ratio): 20

WHSV: 2.5 $hr^{-1}$

The butene conversion changed with the operation time as shown in FIG. 1. The yield of $C_5^{30}$ changed with the reaction time as shown in FIG. 2.

It can be seen from the results of FIG. 1 and FIG. 2 that the lifetime of catalyst in the process provided by the present invention is much longer than that of prior art. The process provided by the present invention can be operated for a prolonged running time, therefore, it may have a promising future in commercial application.

What is claimed is:

1. A process for alkylation of an isoparaffin with an olefin comprising contacting an isoparaffin-containing feed with an olefin-containing feed in the presence of a catalyst, wherein said catalyst comprises 30–99 wt % porous support material and 1–70 wt % heteropoly acid having the following chemical formula:

wherein H is hydrogen atom, k is the number of hydrogen atoms, which is an integer of 3 or 4; Y is an atom selected from the group consisting of of P, Si, Ge or As; W is tungsten atom, m is the number of tungsten atoms, which is a positive integer between 0–12; Mo is molybdenum atom, 12-m is the number of molybdenum atoms; O is oxygen atom, n is the number of crystal water molecules, which is any number in the range of >0–10; the temperature of contacting the isoparaffin-containing feed with the olefin-containing feed in the presence of said catalyst is not lower than the critical temperature of the isoparaffin in the feed and at most 300° C.; the pressure of said reaction is not lower than the critical pressure of the isoparaffin in the feed; and said isoparaffin is one or more isoparaffin selected from $C_4$–$C_7$ isoparaffins.

2. A process according to claim 1, wherein n in said chemical formula of heteropoly acid is any number between 0.5–6.

3. A process according to claim 1, wherein said catalyst comprises 45–95 wt % porous support material and 5–55 w % heteropoly acid.

4. A process according to claim 1 wherein said porous support material is selected from the group consisting of active carbon, silica, alumina, zeolites, carbon fiber, clay and mixtures thereof.

5. A process according to claim 4, wherein said porous support material is selected from the group consisting of active carbon, silica, alumina and zeolites and mixtures thereof.

6. A process according to claim 5, wherein said porous support material is selected from the group consisting of active carbon, silica or alumina.

7. A process according to claim 1 wherein the specific surface area of said catalyst is more than 100 $m^2/g$.

8. A process according to claim 1, wherein Y in the chemical formula of said heteropoly acid is phosphorus atom or silicon atom.

9. A process according to claim 1, wherein said isoparaffin is selected from the group consisting of $C_4$–$C_6$ isoparaffins and said olefin is selected from the group consisting of $C_3$–$C_6$ mono-ethylene unsaturated olefins.

10. A process according to claim 9, wherein said isoparaffin is isobutane and said olefin is selected from the group consisting of propenes, butenes or mixtures thereof.

11. A process according to claim 1, wherein the temperature of contacting said isoparaffin-containing feed with an olefin-containing feed in the presence of said catalyst is 135–250° C.; the reaction pressure is 36–110 atm; the mole ratio of isoparaffin to olefin is 2.0–100; and the WHSV of the feed is 0.1–20 $hr^{-1}$.

12. A process according to claim 11, wherein the reaction temperature is 135–200° C.; said reaction pressure is 36–90 atm; the mole ratio of isoparaffin to olefin is 10–90; and the WHSV of the feed is 0.5–8 $hr^{-1}$.

* * * * *